United States Patent [19]
Caupin et al.

[11] Patent Number: 6,071,472
[45] Date of Patent: Jun. 6, 2000

[54] PROCESS AND DEVICE FOR THE ANTI-ODOR TREATMENT OF AIR

[75] Inventors: M. Henri-Jean Caupin, Versailles; M. Joseph Dussaud, Pont Eveque, both of France

[73] Assignee: Elf Atochem S.A., France

[21] Appl. No.: 09/099,342

[22] Filed: Jun. 18, 1998

[30] Foreign Application Priority Data

Jul. 4, 1997 [FR] France ................................ 97 08522

[51] Int. Cl.[7] ........................................ A61L 9/20
[52] U.S. Cl. ..................... 422/4; 422/5; 422/24; 422/121; 422/122; 55/385.1; 55/524; 95/285; 96/224; 96/226
[58] Field of Search ................ 422/4, 5, 24, 28, 422/121, 122; 55/385.1, 524; 95/285; 96/224, 226

[56] References Cited

U.S. PATENT DOCUMENTS 5,078,971  1/1992  Matuda et al. .......................... 422/121

FOREIGN PATENT DOCUMENTS

| 781562 | 7/1997 | European Pat. Off. . |
|---|---|---|
| 2655878 | 6/1991 | France . |
| 2742663 | 6/1997 | France . |
| 2-242999 | 9/1990 | Japan . |
| 6-134227 | 10/1992 | Japan . |
| 95/17634 | 6/1995 | WIPO . |
| 96/37281 | 11/1996 | WIPO . |
| 97/09073 | 3/1997 | WIPO . |

OTHER PUBLICATIONS

"Desodorisation de L'Air Par Photocatalyse", P. Picat, articles of the Congres Eurodeur [Eurodour Congress] 97, Jun. 25–26, 1997, Paris.

*Primary Examiner*—Elizabeth McKane
*Attorney, Agent, or Firm*—Bell, Boyd & Lloyd PLLC

[57] ABSTRACT

The photocatalytic action of titanium dioxide and the anti-odor activity of undecylenic acid or its compounds are combined in an atmospheric scrubbing or renewal system. The invention consists in placing a filter impregnated with these two substances and exposed to a natural or artificial source of ultraviolet radiation in the path of the air.

5 Claims, No Drawings

PROCESS AND DEVICE FOR THE ANTI-ODOR TREATMENT OF AIR

FIELD OF THE INVENTION

BACKGROUND OF THE INVENTION

The present invention relates to the treatment of olfactory nuisances and to the puri-fication of air, both in open environments and in confined spaces.

The deodorization of atmospheres is a complex problem which has still not been satisfactorily solved. The most effective method still consists of bulk renewal of air in confined spaces, with hourly flow rates of 3 to 5 times per hour in densely populated locations, this situation being aggravated by uncontrollable smoking of tobacco. The effects of this on individuals are known, the least serious of these effects being the impregnation of clothing, the skin and the hair, the most worrying being the effects on public health, and those which can be numerically assessed most immediately being the energy costs to renew the atmosphere, both in terms of heating in winter and airconditioning in summer.

It is known (see P. Pichat, articles of the Congrès Eurodeur [Eurodour Congress] 97, Jun. 25–26, 1997, Paris) that titanium dioxide ($TiO_2$) develops photocatalytic activity under the effect of ultraviolet radiation, which, in the presence of air, generates "O*" free radicals. These free radicals attack chemical compounds adsorbed onto the surface of the $TiO_2$ and, by a sequence of chemical reactions involving atmospheric oxygen, degrade their organic carbon to the ultimate stage of $CO_2$. This activity has been exploited for the destruction of olfactory nuisances in various air-purifying devices. However, this photocatalytic action of $TiO_2$ relies on slow overall kinetics and the odours which it is desired to destroy disappear only after a certain delay period from the moment at which the treatment is started.

It is also known that undecylenic molecules (undecylenic acid, its salts and esters, undecylenyl alcohol, undecylenaldehyde and their immediate chemical derivatives)— referred to hereinbelow as "undecylenic derivatives"— develop a powerful anti-odour activity at low doses on organic substances perceived as being very unpleasant, for example the decomposition products of animal dejecta (see FR-A-2,655,878). This property has been applied for deodourizing cardboard and paper (see FR-A-2,742,663). However, problems of persistance of this activity arise with paper filters simply impregnated with undecylenic derivatives, the nauseating and charged gases which wash against them or cross them also abounding in fatty substances whose accumulation blocks the porosity of the filter and inhibits the molecules of undecylenic derivatives by drowning them in a greasy magma.

DESCRIPTION OF THE INVENTION

It has now been found that it is possible to overcome these drawbacks by preparing paper filters charged or impregnated both with $TiO_2$ and with an undecylenic derivative, and by fitting these filters into ventilation systems in which they are also irradiated by a source of ultraviolet rays when they are not themselves exposed to a natural source of UV.

In order to prepare the filters which are the means of the invention and which themselves form an integral part of the invention, from 3 to 10 g/m² of $TiO_2$ and from 3 to 20 g/m² of undecylenic derivative are bound to surfaces of porous supports, for example sheets of non-sized paper of high porosity, embossed paper plates or a nonwoven of large mesh size.

The cooperation of $TiO_2$ and of the undecylenic derivative in the functioning of the filters of the invention proves to be surprisingly effective from the point of view of air quality and, in parallel, a very substantial increase in the lifetime of the filter is observed, the gradual soiling of which appears to be due essentially only to the retention of inorganic particles. The treated air is immediately of good quality, as soon as the system is put into operation.

Assaying of the remaining undecylenic derivatives in the filter after a certain period of operation is one means of controlling the degree of possible leaching of the product over time, and the maximum possible concentrations of the undecylenic derivatives in the atmosphere.

The invention applies to any form of control of a confined atmosphere with human or animal respiratory cycles. It will find an advantageous application in the air conditioning of motor vehicles, the ventilation of train carriages, especially smoking compartments, airframes, restaurants and in the equipment of kitchen extraction hoods with internal recycling, this list being in no way limiting.

EXAMPLE

The ventilation grille of a low-ceiling nightclub venue with a volume of about 120 m³, which has a high occupation density of smokers, was fitted with a sheet of A4 paper impregnated with 5 g/m² of $TiO_2$ and 3 g/m² of undecylenic acid and a device for UV irradiation of this sheet. Protection against the build-up of odours was thus provided for 7 successive evenings, and it was only after this period that it could be observed that the sheet of impregnated paper was turning black. Throughout this period, the nightclub clientele were able to note that the tobacco smells had disappeared from the atmosphere, which was in stark contrast with the observations made with the initial equipment.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. Process for purifying air, comprising placing a filter impregnated with $TiO_2$ and with an undecylenic compound, irradiated by a source of ultraviolet radiation, in an air renewal circuit or a ventilation machine.

2. Process according to claim 1, wherein a filter impregnated with $TiO_2$ in a proportion of 3 to 10 g/m² and with an undecylenic compound in a proportion of 3 to 20 g/m² is used.

3. Process according to claim 1, wherein the filter consists of a sheet of non-sized paper, a structure made of embossed paper, or a nonwoven.

4. Air filter comprising, a sheet of non-sized paper, a structure made of embossed paper or a nonwoven, impregnated with $TiO_2$ in a proportion of 3 to 10 g/m² and with an undecylenic compound in a proportion of 3 to 20 g/m².

5. An air purification and circulation device comprising at least one ventilation system which actuates a column of air, in the path of which is placed a filter impregnated with $TiO_2$ and with an undecylenic compound irradiated with a natural or artificial source of ultraviolet radiation.

* * * * *